United States Patent [19]

Cappel

[11] 4,348,207

[45] Sep. 7, 1982

[54] METHOD AND MEANS FOR DETERMINATION OF PREGNANCY

[75] Inventor: Leona R. Cappel, Norco, Calif.

[73] Assignee: Cooper Laboratories, Inc., Palo Alto, Calif.

[21] Appl. No.: 230,108

[22] Filed: Jan. 29, 1981

[51] Int. Cl.³ .................. G01N 33/54; G01N 33/76
[52] U.S. Cl. ................ 23/230 B; 23/915; 23/917; 422/61; 422/102; 424/12
[58] Field of Search ............ 422/102, 61; 424/12; 23/230 B, 917

[56] References Cited

U.S. PATENT DOCUMENTS

| | | | |
|---|---|---|---|
| 3,579,306 | 5/1971 | Crane | 23/230 B |
| 3,876,376 | 4/1975 | Bauman | 422/102 X |
| 4,003,988 | 1/1977 | Hoff | 23/230 B X |
| 4,071,314 | 1/1978 | Prugnaud | 23/230 B |
| 4,208,187 | 6/1980 | Givner | 23/230 B |
| 4,210,622 | 7/1980 | Soothill | 422/61 |
| 4,235,839 | 11/1980 | Vesterberg | 422/61 X |

FOREIGN PATENT DOCUMENTS 2805003 5/1979 Fed. Rep. of Germany .

Primary Examiner—Sidney Marantz
Attorney, Agent, or Firm—Thomas R. Boland

[57] ABSTRACT

A diagnostic means and method of testing for pregnancy in humans and a test kit incorporating such diagnostic means and ancillary materials. A sample of a patient's first morning urine is added to a test tube containing a known lyophilized reagent. The tube is capped, shaken to mix the contents, and placed upright for one to two hours. The tube is then inverted and compared with positive and negative standard vials to show either agglutination of particles, such as red blood cells, contained therein, in which case the subject is not pregnant, or a failure to agglutinate, in which event the patient is pregnant. The test tube is of sufficient dimension to support capillary action and is formed from, or has its interior surface coated with, a material which is non-wettable to the liquid contained therein.

16 Claims, 3 Drawing Figures

METHOD AND MEANS FOR DETERMINATION OF PREGNANCY

BACKGROUND OF THE INVENTION

The invention relates to a novel diagnostic means and method of testing for pregnancy in humans, and to a test kit incorporating such diagnostic means and ancillary materials.

It has been known for some time that the presence of human chorionic gonadotropin (HCG) of placenta origin in the urine constitutes one of the early indications of pregnancy. Originally, in vivo methods for determining the presence of such HCG were developed, and while consistently accurate they have proved to be unwieldy because of the difficulty of maintaining a large supply of animals of the required age, the need for multiple, time-lapse, injections of test serums, and the attendant delay in obtaining results.

More recently a number of diagnostic methods for determining pregnancy by in vitro determination of HCG in the urine have developed. In general, these tests involve the interaction of a sample of urine to be tested with a reagent resulting in the formation or inhibition of a precipitate or a sedimentation pattern in the test vial, thus providing a qualitative indication of the presence or absence of the telltale HCG.

For example, U.S. Pat. No. 4,071,314 to Prugnaud discloses a pregnancy test of the agglutination inhibition type using lyophilized reagents including antibody sensitized particles, a buffer solution containing a calcium chelating agent, and an antiserum. Test urine is added to a tube containing the reagent and the presence or inhibition of agglutination of the particles is observed. The test is positive if agglutination is inhibited.

U.S. Pat. No. 3,579,306 to Crane discloses a test kit for pregnancy testing wherein a test tube contains dry solid pellets of red blood cells sensitized with HCG, dry pellets of antiserum, and preferably dry solid pellets of a buffer material. Urine is added to the test tube and a positive test is signified by the absence of agglutination.

In performing these and other in vitro methods of the prior art, after the test urine is supplid to a test vial, e.g., a test tube, it is necessary to maintain the test tube in an upright position undisturbed for up to two hours or more incubation. If the tube during that incubation period is jostled or shaken, either intentionally or accidentally, it will usually not be possible to complete the test; the specimen should be thrown away and the test repeated with a new diagnostic unit.

SUMMARY OF THE INVENTION

The invention includes a transparent, tubular container, for example, a test tube or cuvette, having an internal diameter of sufficient dimension to support capillary action of a liquid contained therein. The container is formed from a material which is non-wettable to the contained liquid, or, alternatively, made from any conventional material and adapted so as to have its interior surface coated with such a non-wettable material. Examples of such materials are polyethylene, polypropylene, polytetrafloroethylene and the like.

The test tube is prepared for subsequent use by placing therein a premeasured amount of a suspension of red particles, e.g., red blood cells, or polymeric latex particles, having chemically bonded thereto the beta-chain of human chorionic gonadotropin. The particles are allowed to settle and the supernatant liquid is removed. A premeasured amount of an antiserum, comprising anti-beta human chorionic gonadotropin, is then added to the tube and the water is removed by lyophilization.

Preferably, three of such test tubes are packaged in a kit including samples of positive and negative urine for comparative purposes, along with instructions for use.

The person performing the test simply places two drops of first morning urine into one of the test tubes from the kit, and the same amount of the positive and negative urine supplied with the kit are added respectively to the remaining test tubes. After this initial preparation, the three tubes are capped, shaken to mix the contents, and placed upright in the kit container. The tubes are allowed to remain in that position for one to two hours after which the red particles are settled in the bottom of the tubes. Each test tube is then inverted and the test is read in five minutes to determine whether agglutination of the red particles has occurred. If the red particles remain in the bottom of the tube then the patient is pregnant. If the particles are agglutinated and settle at the miniscus of the liquid in the inverted tube, then the patient is not pregnant.

The actual reaction is one of inhibition. If the urine being tested contains HCG there is a reaction between the HCG and the antibody of the serum so that the antibody is not available to react with the HCG on the reagent, i.e., either red blood cells or latex particles. If there is no HCG in the urine tested, the HCG on the reagent reacts with the antibody of the serum and this is evidenced by agglutination of the reagent.

DETAILED DESCRIPTION OF THE INVENTION

According to the present invention a new method and means for determining the existence of pregnancy is provided. Such a method and means are not only more efficient than prior art concepts, but in using the present invention it is possible to complete the test in spite of any possible disturbance of the test vial or container. Indeed, one may obtain a second reading from the same test unit by repeating the process.

The test tube utilized in this invention is a transparent, tubular container formed from a material which is non-wettable to the liquid contained therein, e.g., a urine sample, or if not entirely non-wettable, the container has at least its interior surface coated with such a non-wettable material. As used herein the term "non-wettable" means a substance which is not susceptible to adhesion or absorption of a liquid when that liquid is in contact with its surface. Examples of such materials are polyethylene, polypropylene, polytetrafloroethylene, and the like.

Figure 1:
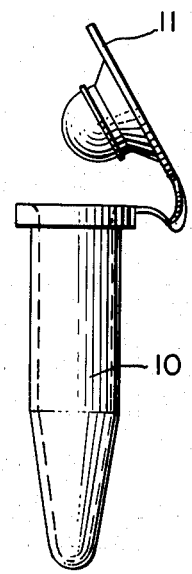
FIG. 1 is a schematic diagram of a test tube useful in this invention showing the test tube in its uncapped configuration.

The container is a relatively tall thin tube, preferably from about one inch to five inches tall, see for example FIG. 1, with an internal diameter of sufficient dimension to support capillary action of the contained liquid, such as urine. That is to say, the internal diameter of the hollow portion of the tube is such that when the tube is inverted, the liquid contained therein will remain in its bottom portion. In a preferred embodiment the test tube has an interior diameter of diminishing scope, for example an interior diameter of 0.6 mm at the opening of the tube, gradually tapering down to an interior diameter of 0.1 mm at the bottom of the tube.

The test tube is prepared to include diagnostic reagents by placing therein a premeasured amount, e.g., 0.05 ml, of a frozen suspension of human chorionic gonadotropin (HCG) chemically coupled to a substrate material such as red blood cells or polymer latex carriers, for example, polystyrene latex particles. Such HCG sensitized blood cells or latex particles may be prepared by conventional methods and are available commercially.

Such a suspension is usually an aqueous dispersion, for example, an aqueous dispersion of colloidal sized particles of an HCG sensitized copolymer wherein the standard size deviation is less than two percent, preferably less than one percent. The particles are allowed to settle in the test tube and the supernatant liquid is removed by any convenient means. A premeasured amount, preferably 0.05 ml, of a frozen antiserum comprising anti-beta human chorionic gonadotropin is then added to the tube so that it is spaced from the sensitized particles and all water is removed by standard lyophilization techniques. Such antiserum is commercially available, and in any case may be produced by means already known to those skilled in the art.

The test tube is then capped by any convenient means, for example, a screw type closure cap or a friction cap, for example, see (11) FIG. 1, made from pliable plastic or rubber, an preferably packaged in a self-contained kit which requires no additional outside equipment for performance of the desired diagnostic test. Such a kit will preferably comprise three of the test tubes including the lyophilized dual-component reagent described above, with positive and negative urine samples, a dropper, and instruction for use.

Figure 2:
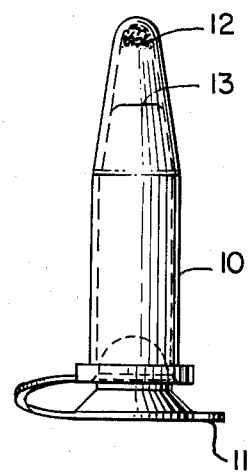
FIG. 2 is a schematic diagram of the test tube in an inverted position showing non-agglutinated particles at the bottom of the tube, signifying that the patient is pregnant.
Figure 3:
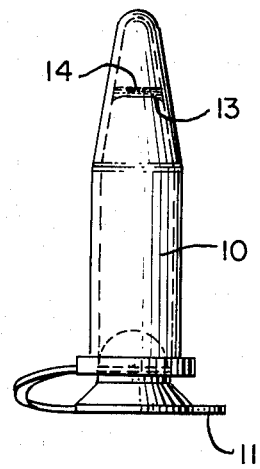
FIG. 3 is a schematic diagram of a test tube according to this invention showing agglutinated particles settled at the miniscus of the liquid in the inverted tube, thus signifying that the patient is not pregnant.

The person performing the test, whether physician clinician, or test subject herself, simply places two drops of first morning urine into one of the test tubes from the kit and a like amount of the comparative samples of positive and negative urine in the remaining test tubes, respectively. The urine may possibly be diluted with a small amount of water, preferably distilled water, i.e., an additional two drops, for example, in each tube. The three tubes are then capped and shaken to mix the contents whereafter they are placed upright in the kit container. The tubes, including the reaction mixture, are allowed to remain in that position for about one-half to two hours, preferably one to two hours, after which the red particles of the mixture will usually be settled in the bottom of the tubes. Each tube is then inverted and the test is read in five minutes to determine whether agglutination of the red particles has occurred. If the red particles remain in the bottom of the diagnostic test tube, for example, see (12) FIG. 2, then agglutination has not taken place because the urine (13) being tested contains HCG which reacts with the antibody of the serum. Consequently, the antibody is not available to react with the HCG on the reagent, i.e., the red blood cells or latex particles. This result indicates that the test subject is pregnant. However, if there is no HCG in the urine being tested, the HCG on the reagent reacts with the antibody of the serum and this is evidenced by agglutination of the reagent. Upon inversion of the test tube, the agglutinated particles settle, see (14) FIG. 3, at the miniscus (13) of the liquid therein indicating that the test subject is not pregnant.

Even if the particles are disturbed during the one to two hours of incubation, it is not necessary to discard the test unit of this invention. In that event, one only needs to allow the reaction mixture to remain at rest for an equal amount of time so that the red particles are settled in the tubes. The tubes are then inverted as indicated above, and the test read in like fashion. If there is any doubt as to the reading, it is also possible according to this invention to simply repeat the process and take a second reading of the same test unit.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A process for diagnosing pregnancy in humans comprising
   providing a test container including a dry reaction mixture comprising HCG sensitized particles and an anti-serum of HCG, said test container having an interior surface, at least, which is non-wettable to urine or a diluting liquid therefor and further having an interior diameter of sufficient dimension to support capillary action of the urine or diluting liquid when contained therein,
   adding a predetermined amount of urine from a subject being tested to the test container and mixing the urine with the reagent contained therein,
   allowing the mixture to stand in the container in an upright position for from about ½ hour to 2 hours,
   inverting the container and inspecting the contents thereof for evidence of an agglutination reaction or inhibition thereof.

2. A process according to claim 1 wherein the HCG sensitized particles are red blood cells chemically bonded to the beta-chain of human chorionic gonadotropin.

3. A process according to claim 1 wherein the HCG sensitized particles are polystyrene latex particles which are chemically bonded to the beta-chain of human chorionic gonadotropin.

4. A process according to claim 3 wherein the standard size deviation of the particles is less than two percent.

5. A process according to claim 1 wherein the test container is formed from a material selected from the group consisting of polyethylene, polypropylene, and polytetrafloroethylene.

6. A process according to claim 1 which further comprises providing two additional test containers along with samples of positive and negative urine for comparative purposes, separately depositing each sample respectively in the additional test containers, allowing the containers to stand, inverting and inspecting the containers as defined in claim 1.

7. A process for diagnosing pregnancy in humans as defined in any one of claims 1 to 6 wherein the interior diameter of the test container is within the range 0.6 mm to 0.1 mm.

8. A diagnostic means for use in detecting the existence of pregnancy in humans, comprising (1) a transparent container having an opening at one end and a cap for said opening, said container having (a) an interior surface, at least, which is non-wettable to urine or a diluting liquid when contained therein, and (b) an interior diameter of a dimension which is effective in supporting said urine and diluting liquid in a bottom portion of the container when the container is inverted, and (2) an effective amount of a reaction mixture adapted to detect the presence or absence of HCG in urine when such urine is added thereto.

9. A diagnostic means as defined in claim 8 wherein the container is formed from a material selected from the group consisting of polyethylene, polypropylene and polytetrafloroethylene.

10. A diagnostic means as defined in claim 8 wherein the reaction mixture includes HCG sensitized particles and an anti-serum of human chorionic gonadotropin.

11. A diagnostic means as defined in claim 10 wherein the HCG sensitized particles are red blood cells chemically bonded to the beta-chain of human chorionic gonadotropin.

12. A diagnostic means as defined in claim 10 wherein the HCG sensitized particles are polystyrene latex particles which are chemically bonded to the beta-chain of human chorionic gonadotropin.

13. A diagnostic means as defined in claim 12 wherein the standard size deviation of the particles is less than two percent.

14. A means for diagnosing pregnancy in humans as defined in any one of claims 8 to 13 wherein the interior diameter of the test container is within the range 0.6 to 0.1 mm.

15. A test kit for early detection of pregnancy in humans conprising diagnostic means as defined in any one of claims 8 to 13, and samples of positive and negative urine for comparative purposes.

16. A test kit as defined in claim 15 which comprises three of the diagnostic means defined in claim 8, positive and negative samples of urine for comparative purposes, and a dropper.

* * * * *